United States Patent
Kim et al.

(10) Patent No.: US 10,274,451 B2
(45) Date of Patent: Apr. 30, 2019

(54) AFFORDABLE ELECTROCHEMICAL DETECTION OF ENVIRONMENTAL CONTAMINANTS

(71) Applicant: Santa Clara University, Santa Clara, CA (US)

(72) Inventors: Unyoung Kim, Palo Alto, CA (US); Silvia Figueira, Campbell, CA (US); Shoba Krishnan, Fremont, CA (US)

(73) Assignee: Santa Clara University, Santa Clara, CA (US)

( * ) Notice: Subject to any disclaimer, the term of this patent is extended or adjusted under 35 U.S.C. 154(b) by 289 days.

(21) Appl. No.: 15/047,185

(22) Filed: Feb. 18, 2016

(65) Prior Publication Data
US 2016/0238555 A1    Aug. 18, 2016

(51) Int. Cl.
| G01N 27/416 | (2006.01) |
| G01N 27/28 | (2006.01) |
| G01N 27/403 | (2006.01) |
| G01N 33/18 | (2006.01) |

(52) U.S. Cl.
CPC ........... *G01N 27/28* (2013.01); *G01N 27/403* (2013.01); *G01N 33/1813* (2013.01)

(58) Field of Classification Search
CPC ............ G01N 27/48; G01N 33/54373; G01N 33/48714; C12Q 1/04; C12M 33/14
See application file for complete search history.

(56) References Cited

U.S. PATENT DOCUMENTS

| 4,625,543 A * | 12/1986 | Ertl ..................... G01N 27/4165 422/82.03 |
| 7,336,362 B2 | 2/2008 | van Geen |
| 8,016,998 B2 | 9/2011 | Compton et al. |
| 2004/0262225 A1* | 12/2004 | C. ............................. B01J 20/06 210/638 |
| 2005/0187097 A1* | 8/2005 | Huang ............... G01N 27/3272 502/101 |
| 2010/0000883 A1 | 1/2010 | Morrin et al. |
| 2010/0307974 A1* | 12/2010 | Pettinger ................... A61L 9/01 210/650 |

(Continued)

FOREIGN PATENT DOCUMENTS

| CN | 1540333 | 10/2004 |
| CN | 102507713 | 6/2012 |

OTHER PUBLICATIONS

Simm et al., "The electrochemical detection of arsenic (III) at a silver electrode", 2005, Electroanalysis v17n19, pp. 1727-1733.

(Continued)

*Primary Examiner* — Gurpreet Kaur
(74) *Attorney, Agent, or Firm* — Lumen Patent Firm

(57) ABSTRACT

This work provides an affordable approach for detecting environmental contaminants (e.g., arsenic in groundwater). Electro-chemical analysis of a sample is performed using a disposable three-electrode sensor that can be connected to an electrochemical analyzer (which is not disposable). The disposable sensor has a sample chamber to admit a liquid sample. The sensor includes a substrate disposed within the sample chamber that includes at least one conditioning reagent to condition the sample for electrochemical analysis. Analysis results can be displayed via a mobile device application.

14 Claims, 7 Drawing Sheets

(56) References Cited

U.S. PATENT DOCUMENTS

2013/0217598 A1    8/2013   Ludwig et al.

OTHER PUBLICATIONS

Dungchai et al., "Electrochemical detection for paper-based microfluidics", 2009, Anal. Chem. v81, pp. 5821-5826.
Godino et al., "Fabricating electrodes for amperometric detection in hybrid paper/polymer lab-on-a-chip devices", 2012, Lab Chip v12, pp. 3281-3284.
Kim et al., "Electrochemical detection of arsenic via a microfluidic sensor and mobile interface toward affordable, rapid and point-of-use water monitoring", Oct. 2013, IEEE 15th conference on Healthcom, pp. 575-579.
Kim et al., "Development of low cost plastic microfluidic sensors toward rapid and point-of-use detection of arsenic in drinking water for global health", Oct. 2013, IEEE conference on Biomedical circuits and systems, pp. 113-117.
Kim et al, "Implementation of electrochemical sensors in arsenic-contaminate areas of West Bengal in India toward rapid and point-of-use detection of arsenic in drinking water", Oct. 2014, IEEE Global Humanitarian Technology Conference, pp. 474-478.
Rowe et al., "CheapStat: an open-source, 'do it yourself' potentiostat for analytical and educational applications", 2011, PLoS ONE v6n9.

* cited by examiner

AFFORDABLE ELECTROCHEMICAL DETECTION OF ENVIRONMENTAL CONTAMINANTS

CROSS REFERENCE TO RELATED APPLICATIONS

This application claims the benefit of U.S. provisional patent application 62/117,745, filed on Feb. 18, 2015, and hereby incorporated by reference in its entirety.

FIELD OF THE INVENTION

This invention relates to detection of environmental contaminants.

BACKGROUND

Detection of contaminants in the environment is important for various applications, but such detection can be difficult and/or costly to perform in practice. The issues involved can be better appreciated by considering the specific application of detection of arsenic in groundwater.

Current solutions for arsenic testing range from simple colorimetric assays to sophisticated laboratory tests. Colorimetric kits, such as the Wagtech Visual Color Arsenic Detection Kit and Arsenator® Digital Arsenic Test Kit, are simple and low-cost, yet generally suffer from a lack of precision, have a higher limit of detection (>10 µg/L), and use toxic chemicals as test reagents. Laboratory-based techniques, such as mass spectrometry, are accurate but considerably more expensive, requiring off-site analysis of samples.

Accordingly, it would be an advance in the art to provide improved low-cost detection of environmental contaminants, such as arsenic in groundwater.

SUMMARY

This work provides an affordable approach for detecting environmental contaminants. Electro-chemical analysis of a sample is performed using a disposable three-electrode sensor that can be connected to an electrochemical analyzer (which is not disposable). The disposable sensor has a sample chamber to admit a liquid sample. The sensor includes a substrate disposed within the sample chamber that includes at least one conditioning reagent to condition the sample for electrochemical analysis. In this way, the user of the system does not have to manually condition the sample for electrochemical analysis. Analysis results can be displayed via a mobile device application.

This approach combines the precision of analytical-grade equipment with a disposable test substrate, resulting in a product that is affordable, accurate, and portable.
Significant advantages are provided:
1) This approach is sensitive (e.g., it can provide a limit of detection for arsenic below the WHO arsenic threshold of 10 µg/L).
2) It can selectively detect the analyte of interest in the presence of competing analytes.
3) It can readily be enclosed in a rugged structure to withstand adverse testing conditions.
4) It costs significantly less than current testing technologies.
5) Its hand held system of phone, analyzer, and sensor provides efficient portability.
6) It eliminates the need for users to handle hazardous chemicals in order to perform tests.
7) It can provide a safe/not-safe analysis result in real time.
8) It can provide a mapping view of environmental contamination.
9) It can be powered and operated through the smartphone (or other mobile device), thereby eliminating the need for separate batteries.

DETAILED DESCRIPTION

Figure 1:
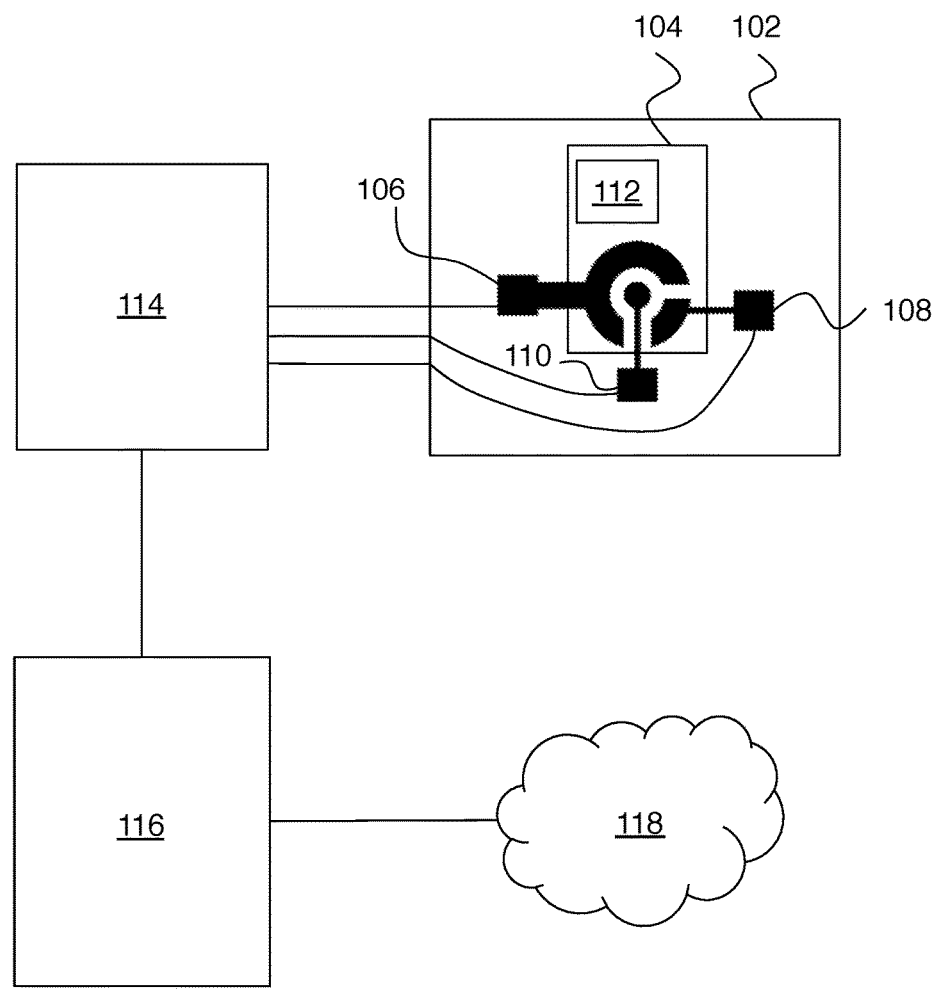
FIG. 1 shows an exemplary embodiment of the invention.

FIG. 1 shows an exemplary embodiment of the invention. In this example, a sensor unit 102 for electrochemical detection of environmental contaminants includes a sample chamber 104 configured to accept a liquid sample, a working electrode 110 disposed in the sample chamber and having a working terminal disposed outside the sample chamber, a counter electrode 108 disposed in the sample chamber and having a counter terminal disposed outside the sample chamber, and a reference electrode 106 disposed in the sample chamber and having a reference terminal disposed outside the sample chamber.

A substrate 112 is disposed in sample chamber 104 that includes at least one conditioning reagent to condition the liquid sample for electrochemical analysis. Sensor unit 102 is configured to make electrical connections between the working terminal, the counter terminal and the reference terminal and an electrochemical analyzer 114 to perform electrochemical analysis of the liquid sample.

Substrate 112 can be a substrate selected from the group consisting of: filter paper, porous cellulose, glass, nitrocellulose, silk and cotton. The conditioning reagent can be an acid or an alkali. Sample conditioning can include altering the pH of the sample by setting the pH to a predetermined value, which can be either acidic or basic depending on details of the electrochemistry to be performed.

Sensor unit 102 is preferably configured for single use operation. In other words, it is preferably disposable.

Sensor unit 102 can be configured for various environmental contaminants, including but not limited to: arsenic ions, nitrate ions, phosphate ions, fluoride ions and bacteria. The environmental contaminants can be measured in samples of groundwater.

In cases where the sensor unit is configured for detection of arsenic ions, the working electrode is preferably carbon, the counter electrode is preferably silver and the reference electrode is preferably a mixture of silver and silver chloride.

In cases where the sensor unit is configured for detection of nitrate ions, the working electrode is preferably copper, the counter electrode is preferably silver and the reference electrode is preferably a mixture of silver and silver chloride.

In cases where the sensor unit is configured for detection of phosphate ions, the working electrode is preferably gold-electroplated carbon, the counter electrode is preferably silver and the reference electrode is preferably a mixture of silver and silver chloride.

More generally, other materials can be used for these electrodes, including but not limited to: carbon, silver, a mixture of silver and silver chloride, gold-plated carbon, and copper.

The geometry/materials of electrode configuration could be modified for better performance or for contaminants other than arsenic. For instance, for the detection of nitrate, copper electrodes can be used as a working electrode. The materials for substrates could be modified for better performance and better adhesion between electrode inks and substrates, such as polyester or cellulose films.

A rugged plastic case can be used to enclose the sensor and it can include a card edge reader to smoothly integrate the sensor with the electrochemical analyzer.

Some embodiments of the invention include only the sensor unit 102. Other embodiments of the invention also include electrochemical analyzer 114. Such systems can further include a mobile device 116 connected to the electrochemical analyzer 114 and having a user interface. Electrical power to the electrochemical analyzer 114 can be provided by the mobile device 116. The user interface of the mobile device can provide various functions. For example, the user interface can include a web-based archive of measurement results. Test results can be transferred to a mobile phone and tagged with GPS coordinates. The data is preferably instantly transmitted to a central database (e.g., in internet 118) where it can be accessed remotely.

Figure 2:
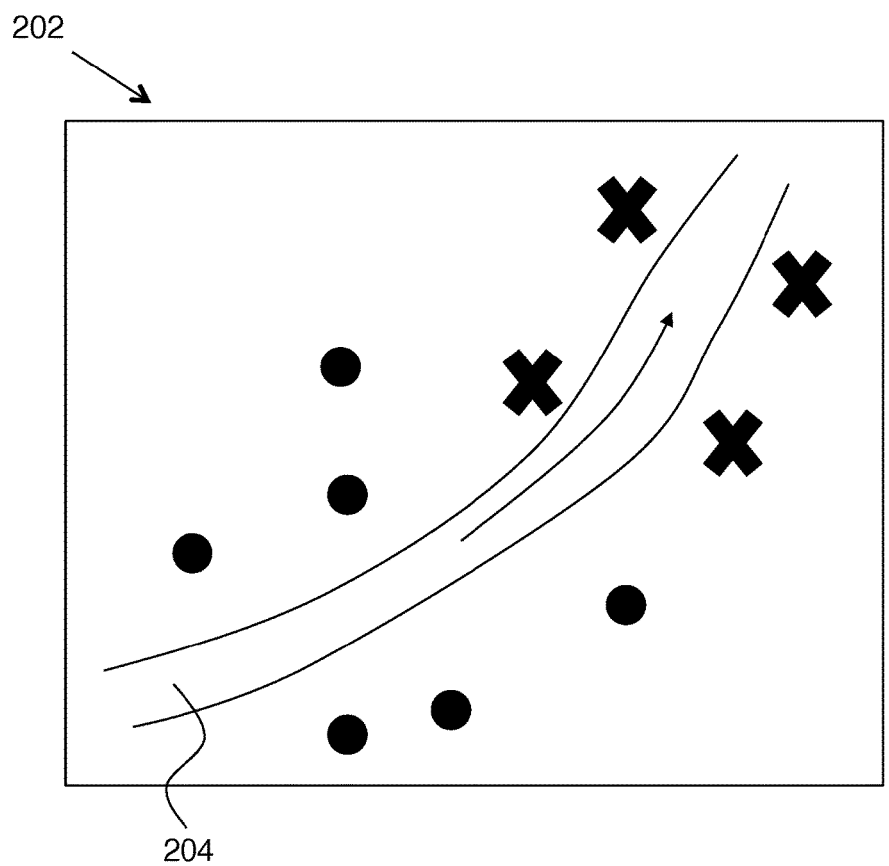
FIG. 2 shows an exemplary mapping of environmental contamination, as may be displayed by embodiments of the invention.

Another possible function for this user interface is to provide mapping of environmental contamination. FIG. 2 schematically shows an example, where display 202 shows measured contamination results near a river 204 via 'safe' icons (black circles) and 'not-safe' icons (black crosses). Here each icon relates to a measurement performed at the location corresponding to its position on the display map. Here the circles and crosses amount to an automatically provided safety determination based on measurement results.

One application of such a system is affordable, disposable, and point-of-use measurement of trace amounts of arsenic in groundwater. The system fulfills a need to quantitatively measure arsenic levels in remote and impoverished regions, where arsenic contamination is of great concern. The sensor can be integrated with a handheld electrochemical analyzer to run a voltammetric scan on a water sample deposited on the sensing region. The output from the analyzer can be sent to a mobile phone application to create a system for real-time distributed water quality monitoring. The phone can process the data received from the analyzer, calculate the level of contamination, which is shown to the user on the spot, along with a safe or not-safe result. From the phone, the data can be sent to a web server, which agglomerates data from different spots and provides a water contamination mapping view.

The sensor can employ a three-electrode system with inkjet-printed conductive ink electrodes. The electrodes can be printed onto a polyethylene terephthalate substrate, providing a rigid and durable platform that remains cost-effective and can be easily disposed of. The electrode-patterned substrate is in contact with a piece of paper pre-dried with reagents to condition the water sample into an appropriate acidic solution, which eliminates the need for users to handle hazardous acids. When the device is connected to the potentiostat and the water sample deposited onto the detection zone, cyclic voltammetry and anode stripping voltammetry can be applied to the electrode surface, producing a current peak for any reducible analytes through the range of the potential scanned.

Practice of the invention does not depend critically on details of the electrochemical analyzer 114. This analyzer can be the interface between sensor 102 and the cellular phone or other mobile device 116. Analyzer 114 preferably incorporates front-end analog circuitry, a mixed-signal microcontroller and a phone interface. The microcontroller initiates the stimulus onto a signal conditioning circuit that performs a voltage sweep on the sensor electrodes. The current output from the sensor electrodes is passed through a current to voltage converter. The output signal is then conditioned and filtered for analysis in the microcontroller where it is converted using an analog to digital converter to data values that can be stored. These digital values are then passed on to the mobile device. This entire system can be powered by the phone, which eliminates the need for batteries. The control of this analyzer is also preferably through a user interface on the smartphone, making it more accessible.

Practice of the invention also does not depend critically on the user interface used for the system. As indicated above, it is preferred for this user interface to be via a smart phone or other mobile device. The main goal of the user interface is to show the end result (safe or not safe to drink) instantly to the user by automatically interpreting the results from the data obtained and making a decision based on water safety guidelines. In an experiment, the interface was implemented for the Android phone because of its recent spread through under-served communities around the world. The phone can communicate with the electrochemical analyzer unit 114 through a USB cable. After each experiment, the data can be uploaded to the phone as a table of voltage measurements. The app can process the data and show the results to the user right away. The result can be presented in two formats: as a curve in a graph or as a safe/not-safe guideline.

The app can also keep a log of previous results, which can be shown in a map. For example, red spots can represent places with unsafe water, and green spots can represent places with safe water. In addition, the app may send the location and corresponding result to a web server, which provides both a visual interface through which uploaded measurements are shown in a map, and data analysis capability. Also, since contamination is aggregated in the web server, providing the system with information on the water flow will enable it to predict contamination.

Figure 3A:
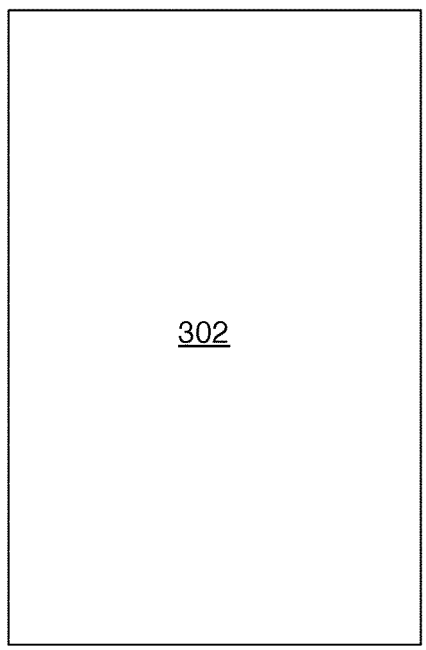
FIGS. 3A-3H show an exemplary assembly sequence for making a sensor according to principles of the invention.
Figure 3B:
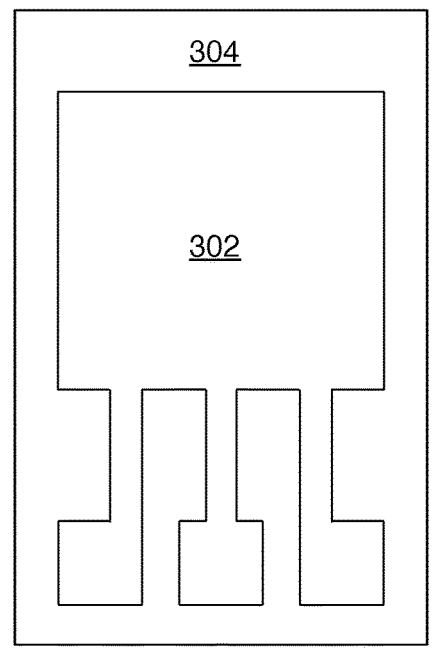
Figure 3C:
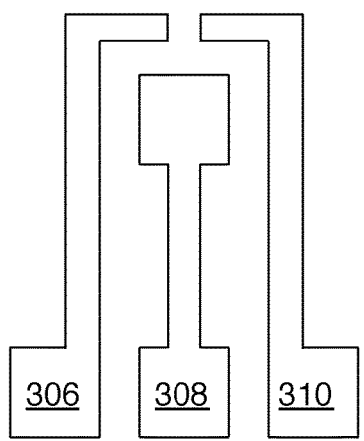
Figure 3D:
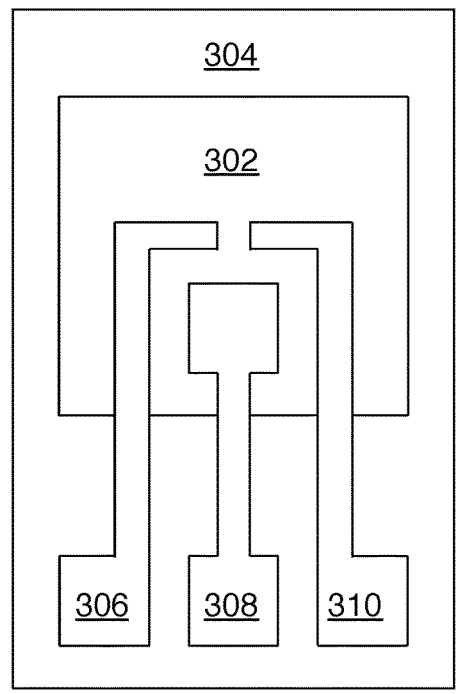

FIGS. 3A-3H show an exemplary assembly sequence for making a sensor according to principles of the invention. FIG. 3A shows base layer 302. This layer supports the device and provides the bottom of the sample chamber. FIG. 3B shows the result of affixing spacer layer 304 to bottom layer 302. Spacer layer 304 has features (as shown) which determine the alignment and spacing of the electrochemical electrodes to ensure consistent results from one sensor to another. FIG. 3C shows counter electrode 306, working electrode 308 and reference electrode 310. FIG. 3D shows the result of inserting the electrodes of FIG. 3C into the alignment features of spacer layer 304 of FIG. 3B. As can be seen, the positions of the electrodes are determined by the features of spacer layer 304.

Figure 3E:
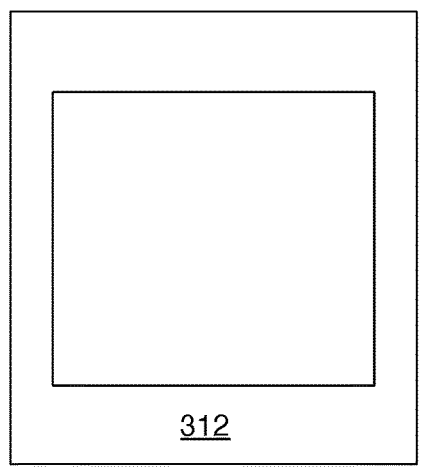
Figure 3F:
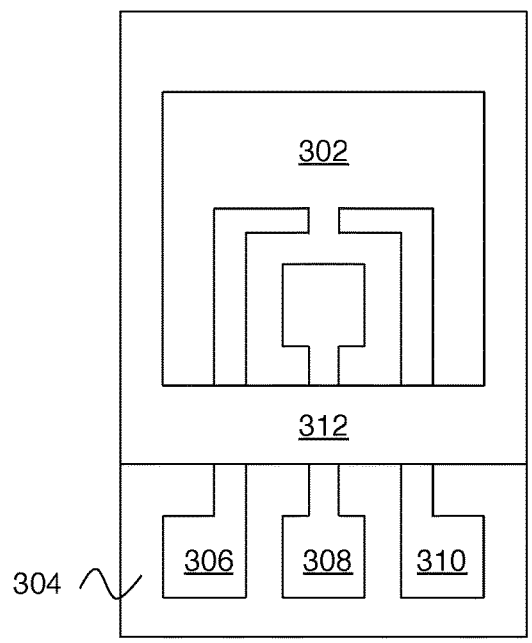
Figure 3G:
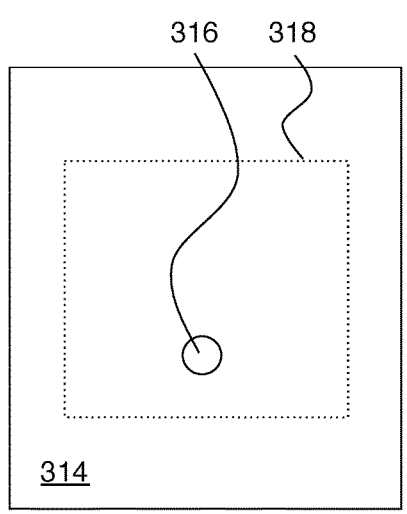
Figure 3H:
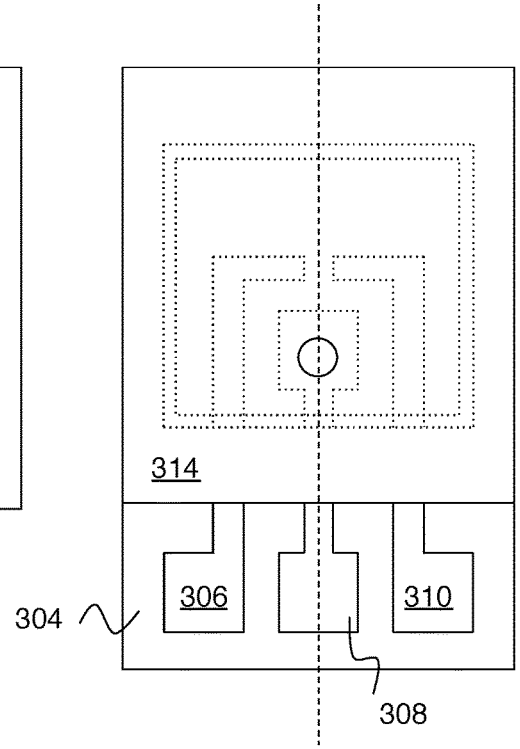

FIG. 3E shows chamber layer 312. This layer provides depth to increase the volume of the sample chamber in the finished device. FIG. 3F shows the result of affixing chamber layer 312 on top of the structure of FIG. 3D. Note that the electrodes are partially exposed to facilitate future electrical connections. FIG. 3G shows top layer 314. The purpose of this layer is to enclose the top of the sample chamber, except for opening 316 for sample introduction. A substrate 318 is affixed to the bottom of top layer 314, and is thus shown with dotted lines on FIG. 3G. Substrate 318 includes one or more sample conditioning reagents to condition the liquid sample for electrochemical analysis. Since this sensor was for arsenic detection, substrate 318 was acidified paper in order to make the sample acidic for electrochemical analysis. FIG. 3H shows the result of affixing top layer 314 to the structure of FIG. 3F. Features which are covered by top layer 314 are shown with dotted lines.

Figure 4:
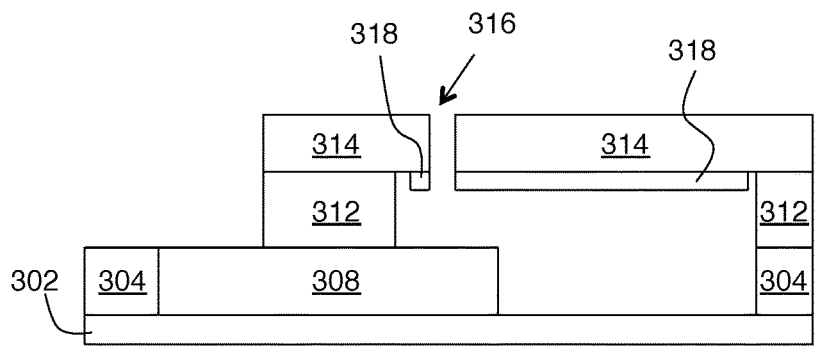
FIG. 4 is a cross section view along the dashed line of FIG. 3H.

FIG. 4 is a cross section view along the dashed line of FIG. 3H. Here it is more apparent how opening 316 is connected to the sample chamber formed by the various layers in the device, and how substrate 318 and the electrodes also extend into this sample chamber.

Practice of the invention does not depend critically on the materials, dimensions or fabrication details of the example of FIGS. 3A-H and 4. Some further details are given below to provide a better appreciation for aspects of the invention. The main goal of this exemplary design was to provide high performance and low cost in a convenient mechanical package.

The layers described above were bonded together using double-sided tape. 3M 444 tape, a polyester film coated with high-tack acrylic adhesive, was selected for its strong bonding capabilities between plastics. The tape adhesive and film are also highly resistant to acid and other solvents, which ensures that the device will not lose structural integrity when an aqueous, acidic sample is added to the test chamber.

As a first step, lengths of 3M 444 double-sided tape (3M Company, Maplewood, Minn.) are applied to sheets of 1/32" thick acrylic plastic (Ridout Plastics Co., Inc., San Diego, Calif.). The protective backing on one side of the tape is left in place. AutoCAD® software (Autodesk, Inc., San Rafael, Calif.) is used to design and accurately dimension the electrodes. The sheets are then laser-cut using an Epilog Zing 40W $CO_2$ laser (Epilog Laser Corp., Golden, Colo.) using a DXF plotting file as input. Sheets of 0.005"-thick Mylar® film (TAP Plastics, Inc., San Leandro, Calif.) and Whatman 1 Chr chromatography paper (GE Healthcare, Little Chalfont, UK) are machined using the laser cutter, as well.

Following the cutting process, 50 μL of 5 M $HNO_3$ is spotted onto each laser-cut square of chromatography paper using a micropipette; the squares are allowed the dry for 1-2 hours. Carbon, silver, and silver-silver chloride conductive inks (C-200/AG-500/AGCL-657, Conductive Compounds, Inc., Hudson, N.H.) are then painted onto the appropriate electrodes cut from acrylic using a small plastic spatula. The electrodes are allowed to dry overnight.

The final step is the bonding of the device layers. The paper squares are affixed to the exposed adhesive on the bottom of the top layer, and the remaining layers are bonded sequentially by simply peeling back the protective film and sticking them together. Once the device is fully assembled, firm pressure is applied manually to the top of the device to ensure strong adhesion between layers.

To summarize, this exemplary design uses 1/32" thick acrylic for top layer 314, chamber layer 312, and spacer layer 304. Electrodes 306, 308 and 310 are painted onto appropriately cut pieces of 1/32" thick acrylic. Base layer 302 is 0.005" thick Mylar®. Base layer 302 is very thin because it is not used to add volume to the device's sample chamber.

Our research has shown that the current design of three electrodes printed onto a plastic substrate is effective in generating a current in the presence of arsenic ions when the sensor is linked to a potentiostat. The height of the current peak is proportional to the arsenic concentration, with samples containing more arsenic ions resulting in higher peaks. In these tests, a carbon working electrode, silver counter electrode, and Ag/AgCl reference electrode was found to be the most effective combination of electrode materials for sensing arsenic. This configuration yielded stripping waveforms that contained well-defined, consistent current peaks.

Figure 5:
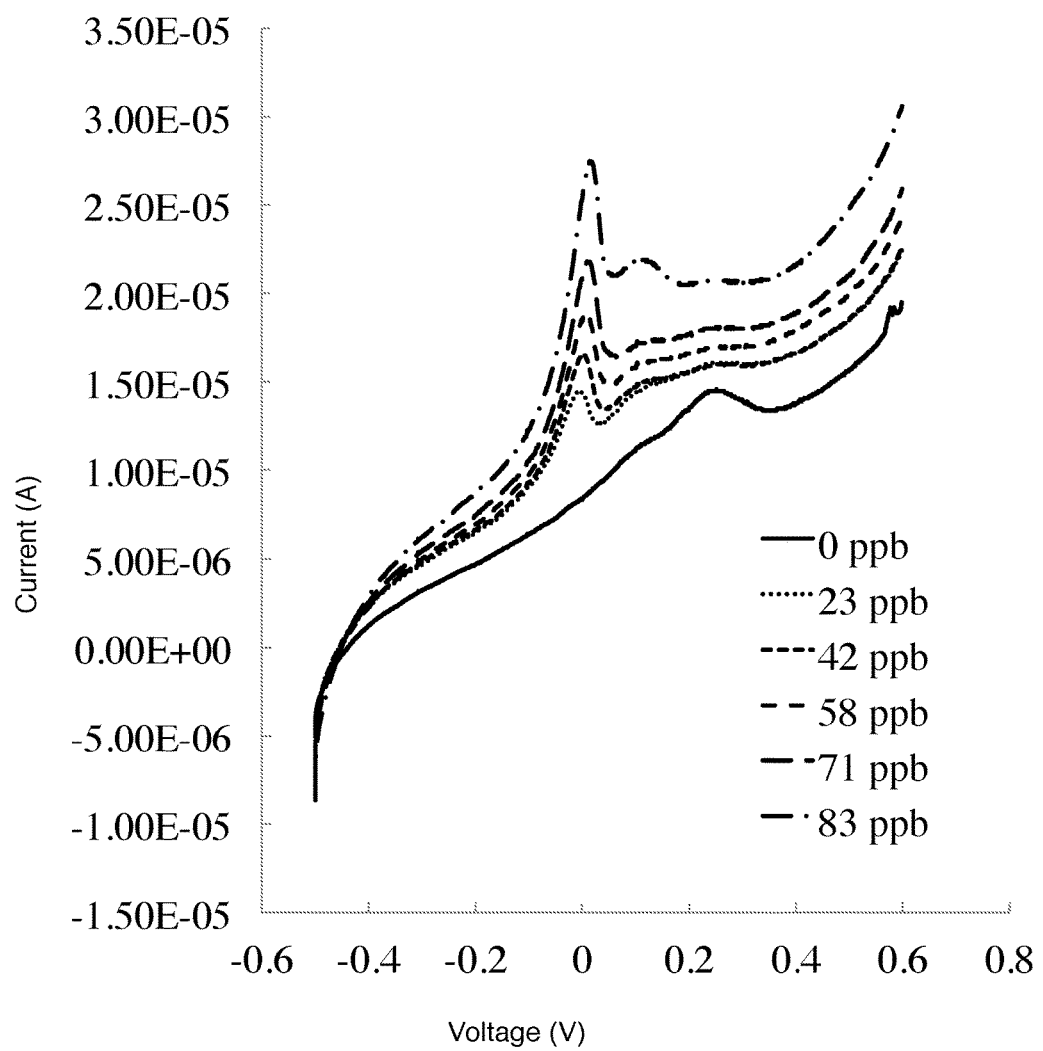
FIG. 5 shows measured arsenic detection according to an embodiment of the invention.

FIG. 5 shows the results of testing to determine the response of our sensing system to known arsenic concentrations. This graph indicates that from concentrations of 23 ppb to 83 ppb, the peak height steadily increased as more arsenic was added. These results tied our tests to specific concentrations within the range we wanted to detect. The control sample, without any arsenic, provides reassurance of the ability of our system to avoid false positives, while the clear peaks in the arsenic-laced samples corroborates its claim to avoiding false negatives.

In a traditional cell-based electrochemical test, an acidic solution is used to ensure adequate electrical conduction between the electrodes. For this type of setup, neutral samples are typically acidified by mixing in a small volume of strong acid. In this work, we aimed to develop a device that is not only portable, but also fully self-contained. Thus, we wished to limit or even completely eliminate the need for acidification of the sample prior to testing.

We have developed a novel solution to the problem of acid pretreatment. Within the electrochemical device, we fixed a small piece of chromatography paper spotted with strong acid and then dried. When a neutral sample solution enters the test chamber and saturates the paper, the sample is acidified to an appropriate level, which simulates the conditions in a glass electrochemical cell.

Paper acidification testing was conducted to determine the volume and molarity of acid with which to pretreat the chromatography paper. The standard cell solution of 0.1 M $HNO_3$, which has a pH of 1, was chosen as the target condition. In these tests, the upper half of an assembled device was spotted with 50 μL of a strong acid of varying molarity (1 M, 5 M, 10 M) and allowed to dry. The pretreated device was mixed thoroughly with 10 mL of DI water in a bottle. The pH of the resulting solution was measured using an Accumet electronic pH meter (Fisher Scientific International, Inc., Hampton, N.H.). This pH value was converted to an equivalent concentration for a test volume of 500 μL, the approximate volume of the device's test chamber.

Table 1 shows the results obtained from paper acidification tests. Single experimental trials were conducted for each acid molarity. The 5 M acid was initially identified as the best candidate, and an additional trial was performed with this molarity to validate the results from the first test. Prior to these tests, the volume of the sample chamber was estimated using a micropipette to add water to the device until completely full. The test yielded an approximate chamber volume of 500 μL, and this value was used to calculate the results in Table 1.

Based on these tests, the 5 M $HNO_3$ acid was selected as the optimal solution for paper pretreatment. The paper squares yielded 10 mL solutions with average pH values of 2.15, equivalent to a molarity of approximately 0.14 M within a device sample chamber. This is reasonably close to the target concentration of 0.1 M, and we do not expect a small difference in solution acidity to affect the quality of results obtained from fabricated devices.

TABLE 1

Results of paper acidification testing

| | pH of solution | Molarity in test tube (M) | Predicted molarity in sample chamber(*) |
|---|---|---|---|
| 1M $HNO_3$ | 2.95 | 0.001122 | 0.02244 |
| 5M $HNO_3$ | 2.14 | 0.007244 | 0.14489 |
| 5M $HNO_3$ | 2.16 | 0.006918 | 0.13837 |
| 10M $HNO_3$ | 1.73 | 0.018621 | 0.37242 |

(*)Assuming a sample chamber volume of 500 μL.

The invention claimed is:

1. A sensor unit for electrochemical detection of environmental contaminants, the sensor unit comprising:
a sample chamber configured to accept a liquid sample;
a working electrode disposed in the sample chamber and having a working terminal disposed outside the sample chamber;
a counter electrode disposed in the sample chamber and having a counter terminal disposed outside the sample chamber;
a reference electrode disposed in the sample chamber and having a reference terminal disposed outside the sample chamber; and
a substrate disposed in the sample chamber that includes at least one conditioning reagent to condition the liquid sample for electrochemical analysis by setting a pH of the liquid sample to a predetermined value;
wherein the sensor unit is configured to make electrical connections between the working terminal, the counter terminal and the reference terminal and an electrochemical analyzer to perform electrochemical analysis of the liquid sample.

2. The apparatus of claim 1, wherein the substrate comprises a substrate selected from the group consisting of: filter paper, porous cellulose, glass, nitrocellulose, silk and cotton.

3. The apparatus of claim 1, wherein the at least one conditioning reagent comprises one or more reagents selected from the group consisting of: acid and alkali.

4. The apparatus of claim 1, wherein the sensor unit is configured for single use operation.

5. The sensor unit of claim 1, wherein the sensor unit is configured for detection of one or more environmental contaminants selected from the group consisting of: arsenic ions, nitrate ions, phosphate ions, fluoride ions and bacteria.

6. The sensor unit of claim 5, wherein the environmental contaminants are measured in samples of groundwater.

7. The sensor unit of claim 1, wherein the sensor unit is configured for detection of arsenic ions, wherein the working electrode comprises carbon, wherein the counter electrode comprises silver and wherein the reference electrode comprises a mixture of silver and silver chloride.

8. The sensor unit of claim 1, wherein the working electrode, the counter electrode and the reference electrode comprise one or more materials selected from the group consisting of: carbon, silver, a mixture of silver and silver chloride, gold-plated carbon, and copper.

9. A system for electrochemical detection of environmental contaminants, the system comprising:
the sensor unit of claim 1;
an electrochemical analyzer electrically connected to the working terminal, the counter terminal and the reference terminal to perform electrochemical analysis of the liquid sample.

10. The system of claim 9, wherein the system further comprises a mobile device connected to the electrochemical analyzer and having a user interface.

11. The system of claim 10, wherein the user interface comprises a mapping of environmental contamination.

12. The system of claim 10, wherein the user interface comprises an automatically provided safety determination.

13. The system of claim 10, wherein the user interface comprises a web-based archive of measurement results.

14. The system of claim 10 wherein electrical power to the electrochemical analyzer is provided by the mobile device.

* * * * *